US009763578B2

(12) United States Patent
Tanaka (10) Patent No.: US 9,763,578 B2
(45) Date of Patent: Sep. 19, 2017

(54) SUBJECT INFORMATION ACQUISITION APPARATUS

(71) Applicant: CANON KABUSHIKI KAISHA, Tokyo (JP)

(72) Inventor: Takatoshi Tanaka, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 157 days.

(21) Appl. No.: 14/527,989

(22) Filed: Oct. 30, 2014

(65) Prior Publication Data

US 2015/0133793 A1    May 14, 2015

(30) Foreign Application Priority Data

Nov. 11, 2013  (JP) .................................. 2013-233331

(51) Int. Cl.
*A61B 5/00* (2006.01)
*A61B 19/00* (2006.01)

(52) U.S. Cl.
CPC .......... *A61B 5/0095* (2013.01); *A61B 5/0062* (2013.01); *A61B 5/6835* (2013.01); *A61B 5/743* (2013.01)

(58) Field of Classification Search
CPC ... A61B 5/0062; A61B 5/0095; A61B 5/6835; A61B 5/743
See application file for complete search history.

(56) References Cited

U.S. PATENT DOCUMENTS

| 6,106,469 A * | 8/2000 | Suzuki ................ G01S 7/52026 600/443 |
| 7,731,662 B2 * | 6/2010 | Anderson ............ A61B 8/0825 600/437 |
| 2012/0257472 A1 | 10/2012 | Yoda ................................ 367/7 |
| 2013/0237801 A1 | 9/2013 | Tanaka .......................... 600/407 |
| 2014/0046166 A1 | 2/2014 | Tokita ........................... 600/407 |

FOREIGN PATENT DOCUMENTS

| JP | 2011-125571 | 6/2011 |
| JP | 2012-231980 | 11/2012 |

* cited by examiner

*Primary Examiner* — Michael Rozanski
(74) *Attorney, Agent, or Firm* — Fitzpatrick, Cella, Harper & Scinto (57) ABSTRACT

A subject information acquisition apparatus comprises a casing in which a transmissive member capable of transmitting acoustic waves and laser beams therethrough is provided; a light irradiating unit disposed inside the casing so as to irradiate a subject with laser beams with the transmissive member interposed; an acoustic wave probe disposed inside the casing so as to receive acoustic waves with the transmissive member interposed; and a scanning mechanism disposed inside the casing so as to move the light irradiating unit and the acoustic wave probe in relation to the casing, wherein the casing is configured to be movable on the subject.

32 Claims, 7 Drawing Sheets

SUBJECT INFORMATION ACQUISITION APPARATUS

BACKGROUND OF THE INVENTION

Field of the Invention

The present invention relates to a subject information acquisition apparatus that acquires information on the inside of a subject.

Description of the Related Art

Studies on a photoacoustic imaging technique of acquiring internal information on a living body using light beams in a non-invasive manner has progressed. When a subject is irradiated with measurement light beams such as pulsed laser beams, the measurement light beams are absorbed by biological tissues inside the subject, and acoustic waves are generated when the biological tissues expand. By receiving and analyzing the generated acoustic waves (also referred to as photoacoustic waves, which are typically ultrasound waves), it is possible to visualize information associated with optical characteristics of the inside of the subject. Such a technique is called photoacoustic tomography (PAT).

In many measurement apparatuses (hereinafter referred to as photoacoustic measurement apparatuses) which use photoacoustic tomography, a configuration in which a probe that receives acoustic waves scans a subject in order to receive acoustic waves from a wide range of areas is employed.

For example, Japanese Patent Application Publication No. 2011-125571 discloses a photoacoustic measurement apparatus of such a type that a subject is sandwiched by two holding members and a probe scans over the surface of the holding member. Moreover, Japanese Patent Application Publication No. 2012-231980 discloses a photoacoustic measurement apparatus of such a type that an operator manually scans the surface of a subject using a portable photoacoustic probe.

SUMMARY OF THE INVENTION

The photoacoustic measurement apparatus of the related art has a problem that the measurement results depend on the operator.

For example, in an apparatus which presses and holds a subject using holding members as in the apparatus disclosed in Japanese Patent Application Publication No. 2011-125571, it is necessary to stretch the subject sufficiently so as to be in close contact with the holding members. If measurement is performed in a state where the subject is not stretched sufficiently, laser beams may not reach up to the deep portion of the subject and the measurement accuracy decreases. Moreover, if wrinkles are formed on the surface of the subject, acoustic waves will be reflected and measurement accuracy may decrease similarly. That is, measurement results change depending on the technique of an operator.

Moreover, when an operator performs manual scanning using a portable probe as in the apparatus disclosed in Japanese Patent Application Publication No. 2012-231980, measurement results change depending on how the probe is moved.

The present invention has been made in view of the problems of the related art, and an object thereof is to provide a subject information acquisition apparatus which can perform measurement easily and of which the measurement results rarely depend on an operator.

The present invention in its one aspect provides a subject information acquisition apparatus comprises a casing in which a transmissive member capable of transmitting acoustic waves and laser beams therethrough is provided; a light irradiating unit disposed inside the casing so as to irradiate a subject with laser beams with the transmissive member interposed; an acoustic wave probe disposed inside the casing so as to receive acoustic waves with the transmissive member interposed; and a scanning mechanism disposed inside the casing so as to move the light irradiating unit and the acoustic wave probe in relation to the casing, wherein the casing is configured to be movable on the subject.

According to the present invention, it is possible to provide a subject information acquisition apparatus which can perform measurement easily and of which the measurement results rarely depend on an operator.

Further features of the present invention will become apparent from the following description of exemplary embodiments with reference to the attached drawings.

DESCRIPTION OF THE EMBODIMENTS

Hereinafter, embodiments of the present invention will be described in detail with reference to the drawings. The same constituent components will basically be denoted by the same reference numerals, and description thereof will not be provided.

First Embodiment

A photoacoustic measurement apparatus according to a first embodiment is an apparatus that irradiates a subject with a laser beam and analyzes acoustic waves generated in the subject due to the irradiation of the laser beam to thereby visualize information associated with optical characteristics of the inside of a living body which is the subject. The information associated with optical characteristics include a generation source distribution of acoustic waves generated due to light beams, an initial acoustic pressure distribution in the subject, an optical absorption coefficient distribution, a concentration distribution of tissue constituting substances, and the like.

<System Configuration>

Figure 1:
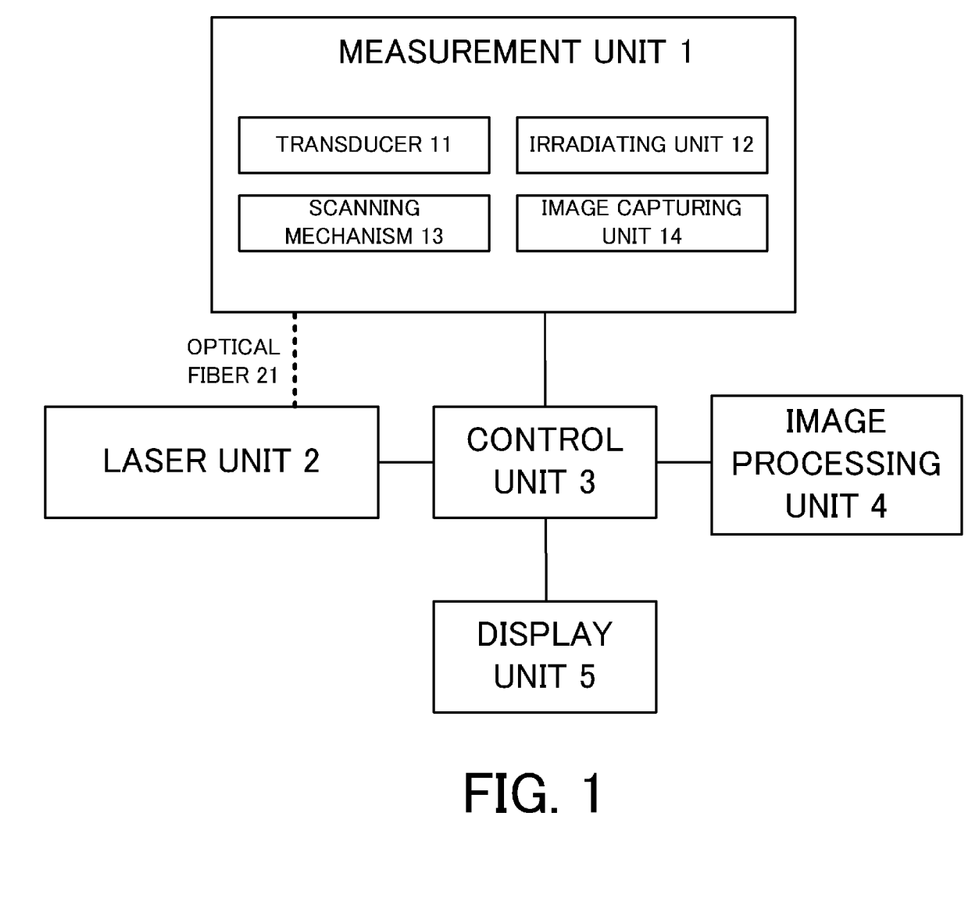
FIG. 1 is a diagram illustrating a system configuration of a photoacoustic measurement apparatus according to a first embodiment.

First, a system configuration of a photoacoustic measurement apparatus according to the first embodiment will be described with reference to FIG. 1. The photoacoustic measurement apparatus according to the present embodiment includes a measurement unit 1, a laser unit 2, a control unit 3, an image processing unit 4, and a display unit 5. Moreover, the measurement unit 1 includes a transducer 11, an irradiating unit 12, a scanning mechanism 13, and an image capturing unit 14.

In the photoacoustic measurement apparatus according to the present embodiment, laser beams generated by the laser unit 2 are guided to the measurement unit 1 to irradiate a subject with the laser beams, and the transducer 11 receives acoustic waves generated inside the subject and converts the acoustic waves into electrical signals. The image processing unit 4 analyzes the electrical signals to thereby obtain information (tomographic images, a distribution of optical characteristic values, and the like) on the inside of the subject.

Hereinafter, the respective units that constitute the photoacoustic measurement apparatus according to the present embodiment will be described.

The laser unit 2 is an apparatus that generates pulse beams to be irradiated to a subject. Although a laser light source is preferably used as a light source in order to obtain a large output power, a light emitting diode, a flash lamp, and the like can be also used instead of the laser. When the laser is used as the light source, various lasers such as a solid laser, a gas laser, a dye laser, or a semiconductor laser can be used.

Moreover, in order to generate photoacoustic waves effectively, it is necessary to irradiate a light beam in a sufficiently short period of time according to thermal characteristics of a subject. When the subject is a living body, approximately 10 to 50 nanoseconds are ideal as a pulse width of the pulsed light beam generated from the light source. Moreover, the pulsed light beam preferably has a wavelength at which light can propagate up to the inside of the subject. Specifically, when the subject is a living body, the wavelength is preferably between 400 nm and 1600 nm, and is more preferably between 700 nm and 1100 nm where little light is absorbed in the living body.

The pulsed light beam generated by the laser unit 2 will be referred to as a measurement light beam.

A light guiding unit 21 is a unit that guides the laser beam generated by the laser unit 2 to the measurement unit 1 and is formed of an optical element or an optical member such as an optical fiber, a mirror, or a prism. When the laser beam is guided using an optical fiber, it is preferable to use a bundle fiber which can transmit a large amount of light and provide flexibility. Moreover, the laser beam may be guided to the measurement unit 1 by air propagation.

The control unit 3 is a unit that controls the photoacoustic measurement apparatus according to the present embodiment. Specifically, the control unit 3 controls light emission of a laser, scanning of the irradiating unit and the transducer, and digital conversion of signals received by the transducer.

The image processing unit 4 is a unit that processes the digital signal converted by the control unit 3 to generate two or three-dimensional image data indicating an absorption coefficient distribution in the subject. Image data can be generated using an existing method such as a phasing addition method or a universal back-projection method in which differentiated signals are superimposed. The generated images are presented to users by the display unit 5 (for example, a liquid crystal display).

The control unit 3 and the image processing unit 4 may be a computer that includes a CPU, a main storage device, and an auxiliary storage device and may be exclusively designed hardware.

Next, constituent components of the measurement unit 1 will be described.

The measurement unit 1 is a unit that irradiates the subject with the laser beam guided by the light guiding unit 21 and receives acoustic waves arriving from the subject.

The transducer 11 is a unit that converts the acoustic waves generated inside the subject into analog electrical signals using an electromechanical conversion element (hereinafter referred to as a conversion element). The transducer 11 is also referred to as an acoustic wave detector, an acoustic wave probe, or simply a probe. Acoustic waves used in the present invention are typically ultrasound waves, and include elastic waves called sound waves, ultrasound waves, photoacoustic waves and photo-ultrasound waves.

Moreover, the transducer 11 preferably has high sensitivity and a wide frequency band. Specifically, transducers formed from piezoelectric ceramics (PZT) and polyvinylidene fluoride resin (PVDF), Capacitive micromachined ultrasonic transducers (CMUT), and Fabry-Perot interferometers can be used. However, the transducer is not limited to these examples but an optional transducer may be used as long as it provides the functions of a transducer.

Moreover, when a three-dimensional image is reconstructed by photoacoustic measurement, it is preferable to use conversion elements arranged in a two-dimensional array in order to decrease directional dependency of image resolution.

The irradiating unit 12 is a unit that irradiates the subject with the measurement light beam. The irradiating unit 12 is formed of an optical member such as a lens, a mirror, a diffuser, or an optical fiber and guides the laser beam guided by the light guiding unit 21 up to the surface of the subject. A specific light guiding method will be described later.

The irradiating unit 12 is a light irradiating unit of the present invention.

The scanning mechanism 13 is a mechanism that moves the irradiating unit 12 and the transducer 11 at least in one direction so as to perform translational and rotational movement.

As a method of receiving acoustic waves from a wide area of the surface of the subject, a method of arranging conversion elements on the entire surface of a target area and a method of mechanically causing a group of relatively small conversion elements to perform scanning using a scanning mechanism may be used. From the perspective of cost effectiveness, the method of using the scanning mechanism is preferred. By performing scanning while moving the transducer 11 and the irradiating unit 12 using the scanning mechanism 13, it is possible to receive acoustic waves at a plurality of positions and to perform measurement on a wide range of areas. A specific arrangement of mechanisms will be described later.

<Structure of Photoacoustic Measurement Apparatus>

Figure 2:
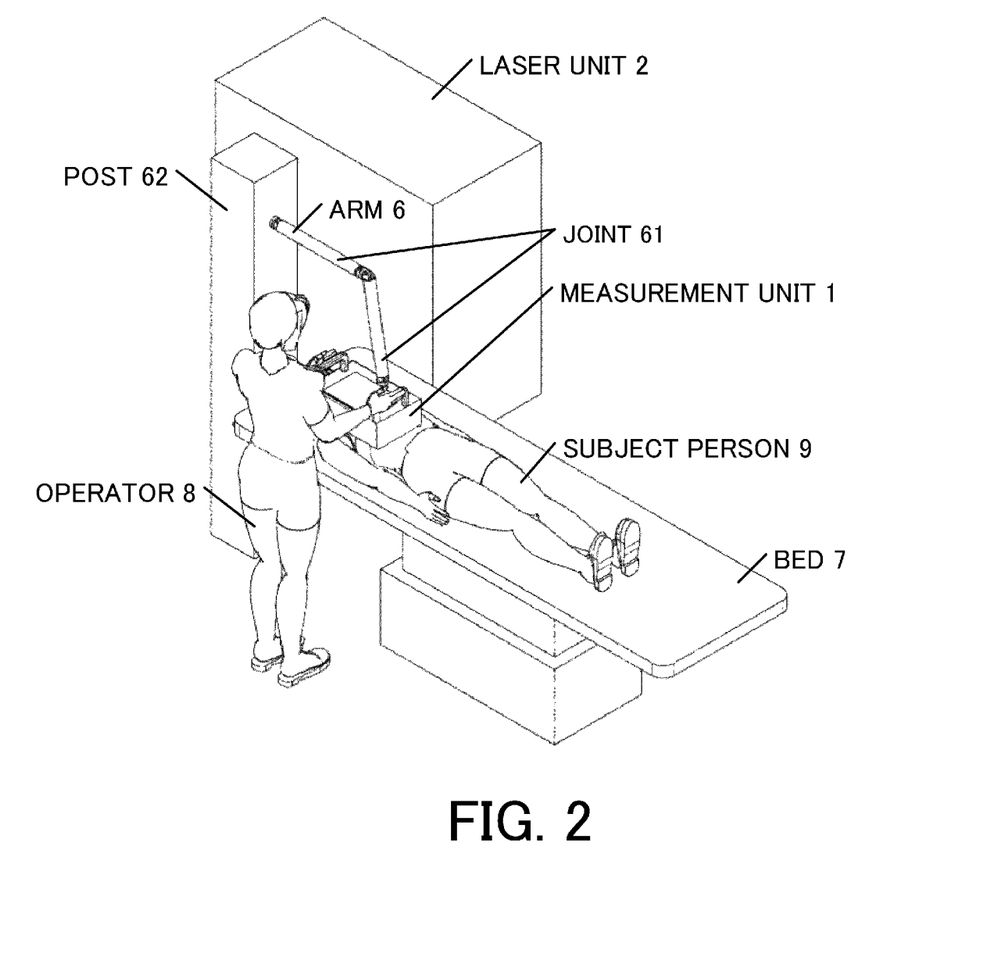
FIG. 2 is a perspective view of the photoacoustic measurement apparatus according to the first embodiment.

Next, the structure of the photoacoustic measurement apparatus according to the first embodiment will be described with reference to FIG. 2 which is a perspective view of the apparatus. The photoacoustic measurement apparatus according to the present embodiment is an apparatus that performs measurement on the breast of a subject person in a supine position.

The measurement unit 1 is connected to a post 62 of the apparatus with an arm 6 interposed. Moreover, the arm 6 has a plurality of joints 61, and due to this, the measurement unit 1 can be moved to an optional position above the subject. The joint 61 may be a joint having a plurality of degrees of freedom and may be one obtained by combining a plurality of joints each having one degree of freedom. Moreover, the arm 6 may have a locking mechanism. Due to this, it is possible to move the measurement unit 1 in three-dimensional directions and to fix the measurement unit 1 in a desired posture in a state where the unit is in close contact with the subject person.

The arm 6 is a supporting mechanism of the present invention.

A bed 7 is a table on which a subject person 9 is placed and is a subject mounting unit of the present invention. The bed 7 has an adjustment mechanism (not illustrated) for adjusting the height and the position of the table so that an operator 8 can easily use the photoacoustic measurement apparatus.

<Structure of Measurement Unit>

Next, the structure of the measurement unit 1 will be described with reference to FIGS. 3 and 4.

Figure 3:
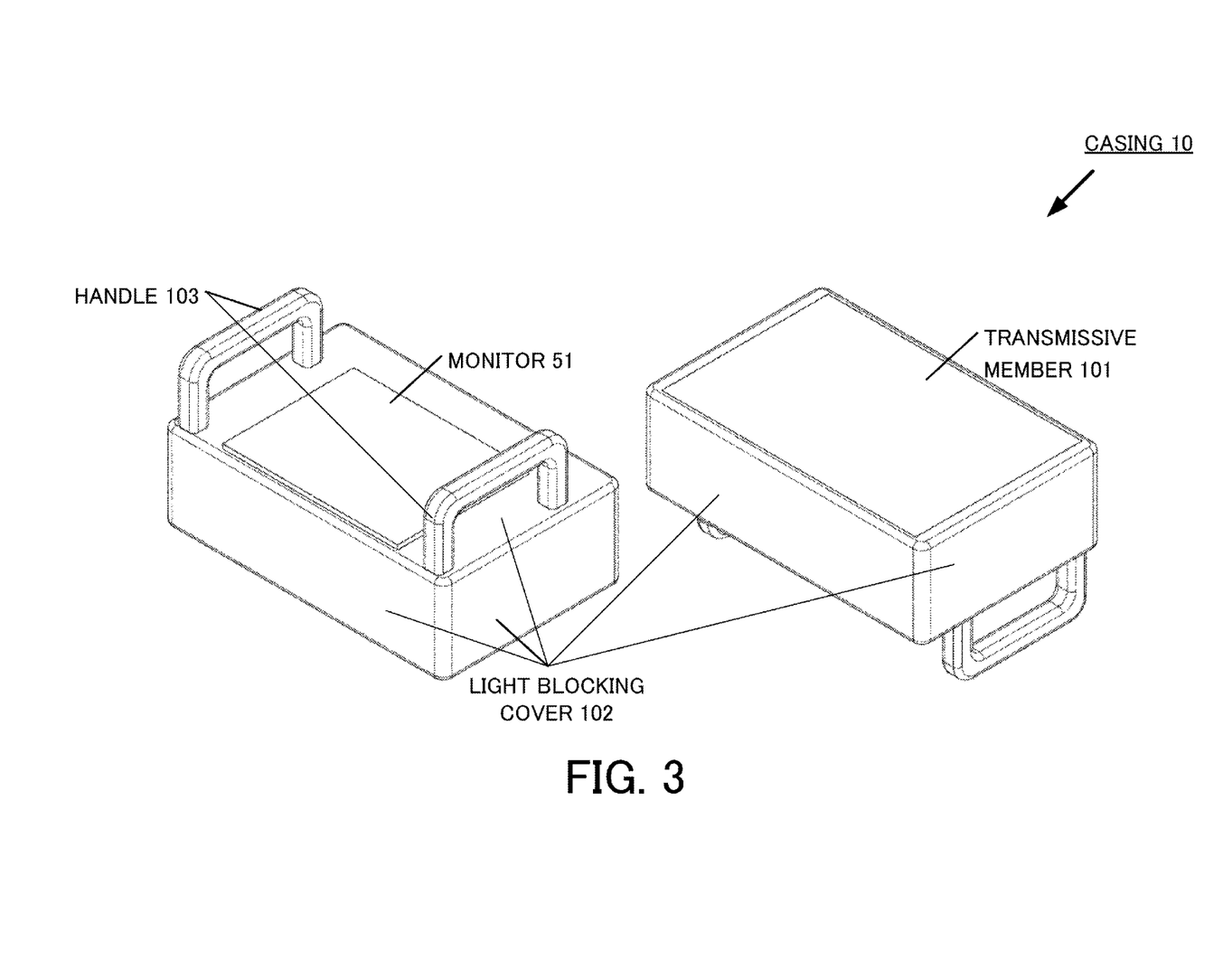
FIG. 3 is a perspective view of a measurement unit according to the first embodiment.
Figure 4:
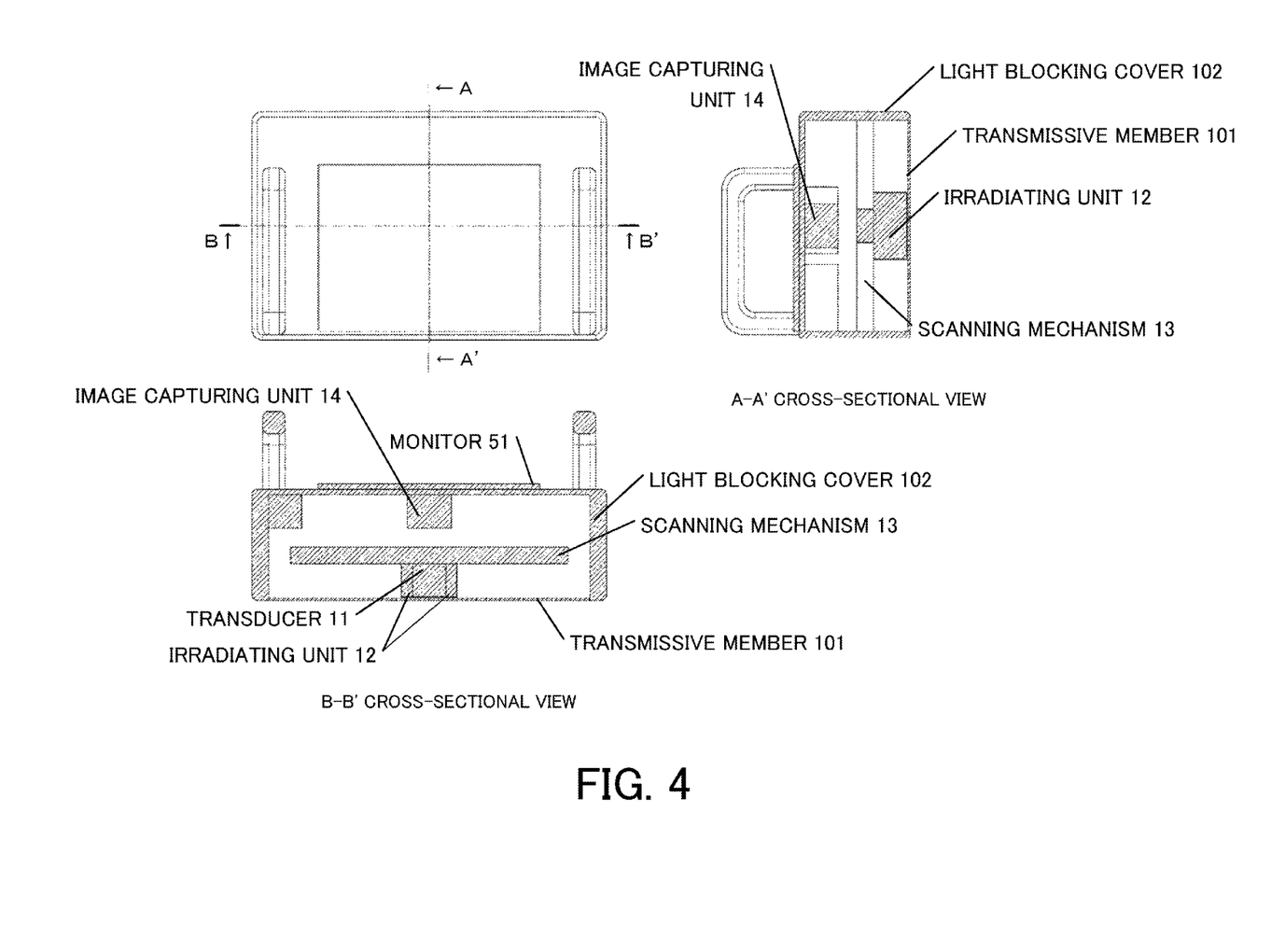
FIG. 4 is a cross-sectional view of the measurement unit according to the first embodiment.

FIG. 3 is a perspective view of the measurement unit 1. Respective constituent components of the measurement unit 1 are stored in a casing 10. The operator grasps handles 103 to move the casing 10 to a desired position of the subject person 9 and performs measurement while pressing the subject person 9 in a desired posture.

The casing 10 includes a transmissive member 101 and a light blocking cover 102. The transmissive member 101 is a portion that makes close contact with a subject segment of a subject person and is formed of a member which transmits the measurement light beam irradiated to the subject and acoustic waves generated from the inside of the subject therethrough. The transmissive member 101 is preferably formed of a member of which acoustic impedance is close to that of a subject. Since the measurement unit is used by being in contact with the subject, by matching the acoustic impedance of the transmissive member with that of the subject, it is possible to suppress acoustic waves from being generated from the surface of the transmissive member 101. Further, the transmissive member 101 is preferably formed of a thin member. In this way, it is possible to suppress attenuation of the generated acoustic waves.

The light blocking cover 102 is a member that has a function of blocking the measurement light beam (that is, a laser beam) irradiated to the subject and is a light blocking member of the present invention. In the present embodiment, portions of the casing 10 other than the transmissive member 101 are formed of the light blocking cover 102. In this way, it is possible to protect the eyes of the operator 8 and the subject person 9 from laser beams.

The light blocking cover 102 may be formed from a material that can at least block the measurement light beam. For example, when the measurement light beam is near-infrared light, a material that does not transmit near-infrared light may be used. Moreover, a material that transmits light having a wavelength other than that of the measurement light beam may be used. For example, the light blocking cover 102 may be formed from a material that transmits visible light and the like. When the light blocking cover 102 is formed from a material that transmits visible light, it is possible to visually perceive the contacting state of the casing and the subject from the outside of the casing.

Further, the casing 10 includes a monitor 51 for checking the state of a portion in which the transmissive member 101 and the subject are in contact. The contacting state of the subject and the transmissive member 101 is displayed on the monitor 51. In this way, the operator can check on an image whether wrinkles are formed in the subject and whether bubbles are present between the subject and the transmissive member 101, for example. A camera that captures images to be displayed on the monitor 51 will be described later.

Next, an inner structure of the measurement unit 1 will be described with reference to FIG. 4 which is a cross-sectional view of the measurement unit 1.

The irradiating unit 12 which is a unit that irradiates the subject with a laser beam and the transducer 11 that receives acoustic waves generated from the subject are incorporated into the measurement unit. Moreover, the scanning mechanism 13 for allowing the irradiating unit 12 and the transducer 11 to perform scanning are incorporated. In this way, it is possible to perform the irradiation of the measurement light beam and the reception of acoustic waves repeatedly while moving the irradiating unit 12 and the transducer 11.

The scanning mechanism 13 is disposed so that the irradiating unit 12 and the transducer 11 are moved along a plane parallel to the transmissive member 101. The irradiating unit 12 and the transducer 11 are preferably mounted on the same stage (not illustrated). This is because, if the irradiating unit 12 is mounted on a different stage from the transducer 11, it is necessary to synchronize the control of the positions of both stages, which complicate the control. Another reason is because, when the transducer 11 only is allowed to scan mechanically and the irradiating unit 12 is fixed, it is difficult to irradiate a sufficiently strong laser beam at a desired position. By mounting both the irradiating unit 12 and the transducer 11 on the same stage, it is possible to always irradiate the measurement light beam near the transducer 11 and to make the apparatus compact.

The measurement unit 1 of the present embodiment has the image capturing unit 14 for capturing the image of a contacting surface of the casing and the subject. The image capturing unit 14 includes a camera that captures the image of the subject surface and an illumination (not illustrated). The camera is disposed on a side opposite the transmissive member 101, as seen from the scanning mechanism 13, at a position where the entire measurement area can be imaged. Although one camera is used in the present embodiment, two or more cameras may be disposed and respective images may be combined. The image captured by the camera is output to the monitor 51 provided on the light blocking cover 102.

The irradiating unit 12 and the transducer 11 are preferably moved outside a capturing area of the camera by the scanning mechanism 13 when measurement is not performed. This is because the irradiating unit 12 and the transducer 11 remaining in a capturing range of the camera are obstacles when observing the subject surface.

The operator 8 can check the contacting state of the transmissive member 101 and the subject while viewing the image displayed on the monitor 51 before starting photoacoustic measurement. For example, when the subject is the breast of the subject person 9, the operator 8 can check whether bubbles are present between the transmissive member 101 and the breast and whether wrinkles are formed on the breast surface and can reinstall the measurement unit as necessary.

When a portion that the operator wants to check in further detail is noticed on the image, the portion may be displayed at an enlarged scale. For example, the monitor 51 may be configured as a touch panel, the displayed image may be enlarged and reduced by a pinch-in/out operation.

Moreover, when photoacoustic measurement is performed, the operator 8 may designate a measurement range using the camera image on the monitor 51. For example, the monitor 51 may be configured as a touch panel and the imaging range may be designated by a touch operation and a drag operation. Moreover, the image generated by the image processing unit 4 may be displayed on the monitor 51 after photoacoustic measurement is completed. That is, the display unit 5 may serve as the monitor 51. By doing so, the operator can check the measurement results while viewing the image on hand.

A liquid for matching acoustic impedance is filled into the casing 10. Examples of such a liquid include water, castor oil, and the like. The liquid preferably has acoustic impedance close to that of the subject similarly to the transmissive member 101. In the first embodiment, this liquid is referred to as an acoustic matching liquid. By matching the acoustic impedance, it is possible to suppress acoustic waves from reflecting from the surfaces of the respective members and to increase the acoustic pressure of the acoustic waves that the transducer receives.

Moreover, when the acoustic matching liquid is filled into the casing, since an acoustic matching material is always interposed between the transducer and the transmissive member, a state where the acoustic impedance of respective members is matched is maintained regardless of the posture of the measurement unit. The casing 10 has such a seal function that the acoustic matching liquid does not leak outside.

Figure 5:
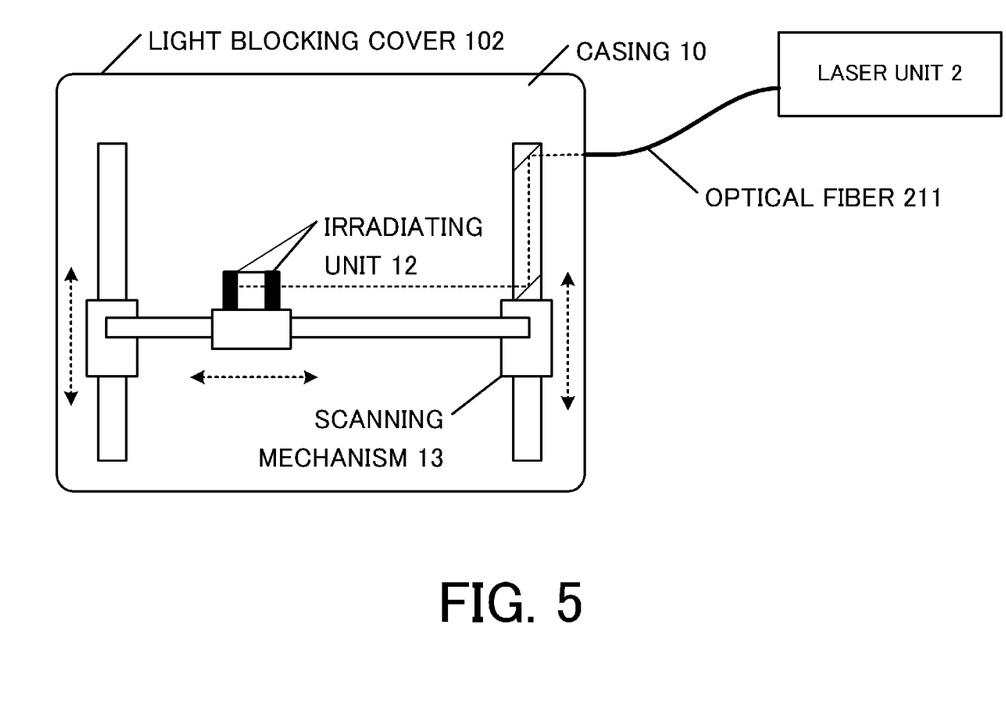
FIG. 5 is a diagram illustrating the path of a laser beam of the measurement unit according to the first embodiment.

Next, the path of a laser beam in the casing 10 will be described with reference to FIG. 5. The laser beam generated by the laser unit 2 is supplied to the measurement unit via an optical fiber 211 which is a light guiding unit. By guiding the laser beam using the optical fiber, it is possible to supply the measurement light beam reliably regardless of the position and the posture of the measurement unit.

The laser beam supplied to the inside of the measurement unit by the optical fiber 211 is guided to the irradiating unit 12 by a mirror or a prism. Although it is not impossible to guide laser beams using an optical fiber disposed inside the casing, since the optical fiber has a large radius of curvature, when the optical fiber is attached directly to the irradiating unit 12 moved by the scanning mechanism 13, a space in which the optical fiber moves needs to be secured in the casing. Thus, in order to make the measurement unit 1 compact, it is preferable to guide the laser beam using mirrors or prisms inside the casing.

According to the first embodiment, since a measuring system is stored inside a casing configured to be freely movable in relation to a subject and is moved in relation to the casing, it is possible to perform measurement in a state where the position of the measuring system is fixed. With this configuration, since it is not necessary to sandwich a portion of the subject unlike the related art, the operator can easily perform measurement. Moreover, since it is possible to perform measurement on a desired range of areas just by pressing the measurement unit against the subject person, the measurement results do not depend on the technique of the operator.

Second Embodiment

A second embodiment is an embodiment in which a unit configured to circulate an acoustic matching liquid filled into the casing of the measurement unit and a unit configured to adjust the temperature of the acoustic matching liquid are added to the first embodiment.

Figure 6:
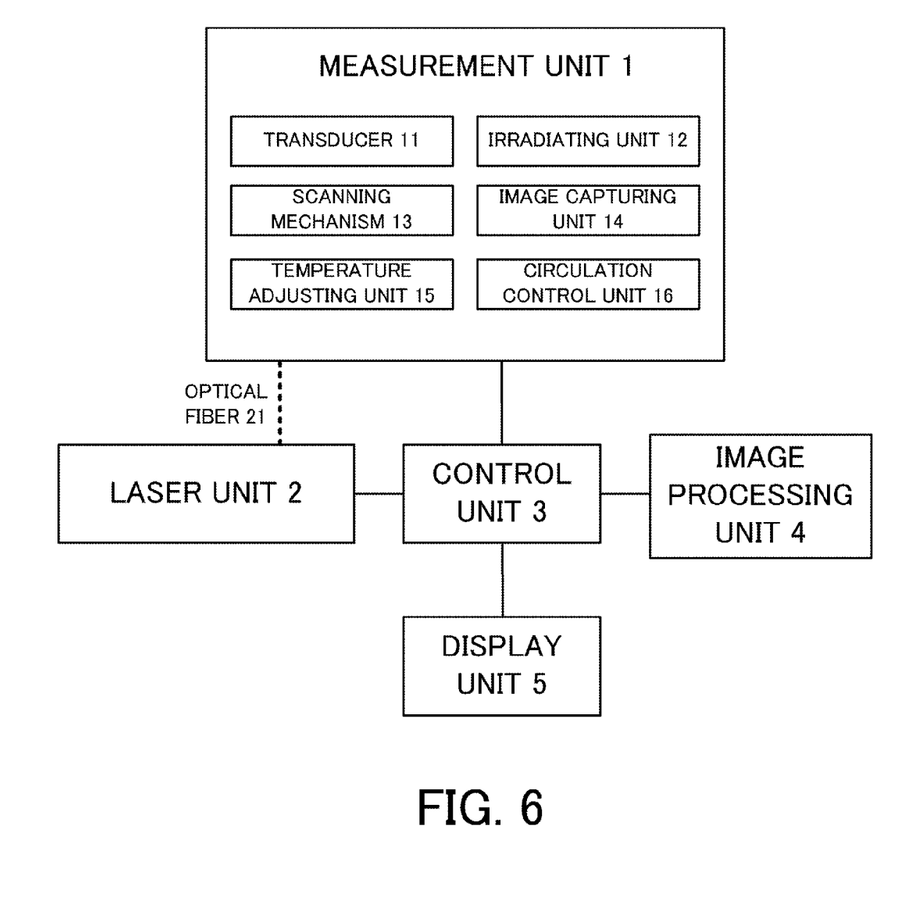
FIG. 6 is a diagram illustrating a system configuration of a photoacoustic measurement apparatus according to a second embodiment.

FIG. 6 is a diagram illustrating a system configuration of a photoacoustic measurement apparatus according to the second embodiment. Constituent components other than a temperature adjusting unit 15 and a circulation control unit 16 are the same as those of the first embodiment.

The temperature adjusting unit 15 is a unit that adjust the temperature of the acoustic matching liquid to a predetermined temperature. For example, the temperature of the liquid is adjusted using an internal heater or the like. The temperature adjusting unit 15 is a temperature adjusting unit of the present invention.

Figure 7:
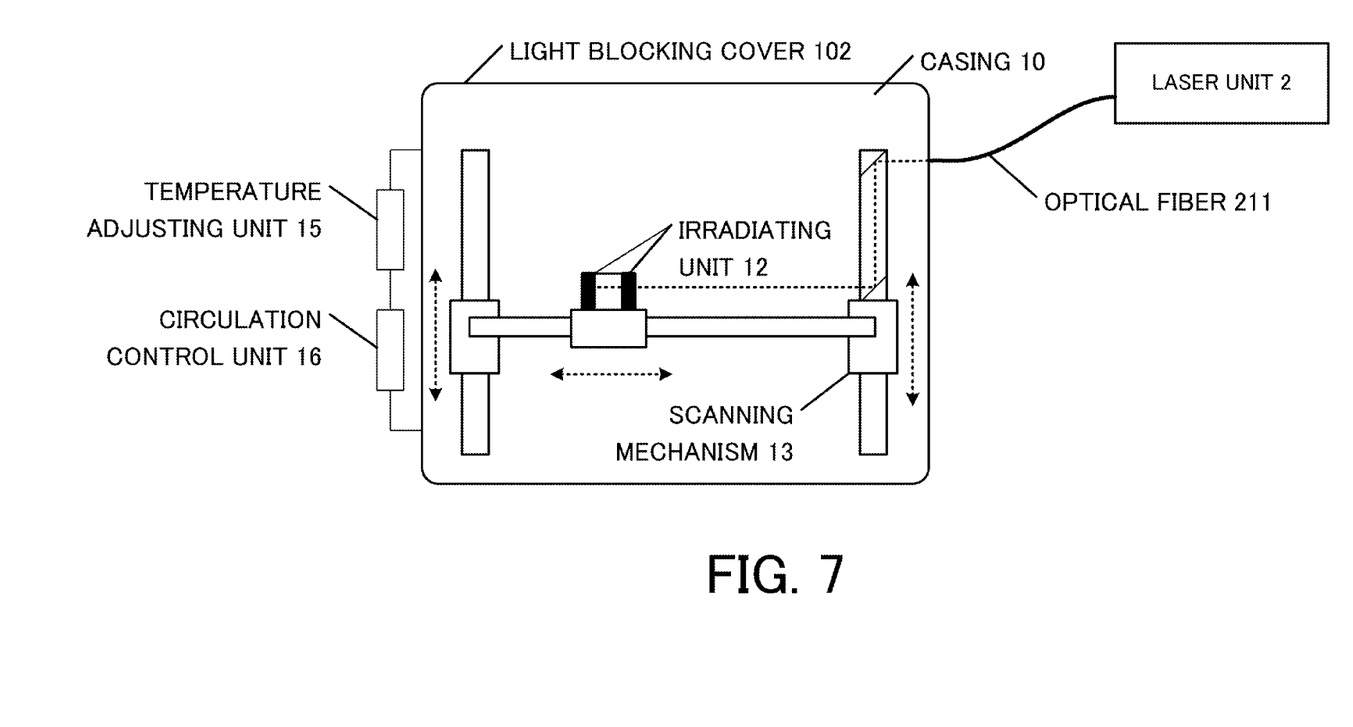
FIG. 7 is a diagram illustrating the path of a laser beam of a measurement unit according to the second embodiment.

Moreover, the circulation control unit 16 is a pump that delivers the liquid heated to the predetermined temperature into the casing. The circulation control unit 16 delivers the acoustic matching liquid with a predetermined flow rate so that the liquid circulates. FIG. 7 is a diagram illustrating the arrangement of the temperature adjusting unit 15 and the circulation control unit 16.

According to the second embodiment, since the temperature of the acoustic matching liquid filled into the casing 10 is adjusted and circulated, the temperature of a propagation path of acoustic waves can be maintained to be constant. Since the speed of acoustic waves change depending on a temperature, it is possible to suppress changes in the measurement results by controlling the temperature of the propagation path of acoustic waves to be constant. Moreover, it is possible to prevent an increase in the temperature of the inside of the casing due to the laser beam. Further, since the temperature of the contacting portion of the measurement unit and the subject person approaches the temperature of the subject person, it is possible to diminish discomfort that the subject person may experience.

(Modifications)

The respective embodiments are examples used for explaining the present invention, and the present invention can be implemented by appropriately changing or combining the respective embodiments without departing from the spirit of the present invention. For example, the present invention can be implemented as a method of controlling the subject information acquisition apparatus, including at least a portion of the processes. The processes and units can be freely combined with each other unless such combinations incur technical conflicts.

For example, although an example of performing measurement on a subject person in a supine position has been illustrated in the embodiments, the subject information acquisition apparatus according to the present invention can perform measurement on a subject person in a prone position, a sitting position, or a standing position. Moreover, the unit on which the subject person is placed may be a bed and may be a chair.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-233331, filed on Nov. 11, 2013, which is hereby incorporated by reference herein in its entirety.

What is claimed is:

1. A subject information acquisition apparatus comprising:
    a hermetic casing having an opaque housing with an opening and a transmissive member secured to the opaque housing;
    an irradiating member disposed inside the hermetic casing so as to radiate light to a subject via the transmissive member;
    an acoustic wave probe disposed inside the hermetic casing so as to receive acoustic waves via the transmissive member propagated from the subject; and a scanning mechanism disposed inside the hermetic casing so as to move the irradiating member and the acoustic wave probe in relation to the hermetic casing, wherein the transmissive member shows a higher optical transmissivity than the opaque housing, and wherein the transmissive member is secured to the opaque housing in liquid tight manner around the opening so as to store an acoustic matching liquid therein.

2. The subject information acquisition apparatus according to claim 1, further comprising:
a subject mounting unit on which the subject is placed, wherein the hermetic casing is configured to be movable in relation to the subject mounting unit.

3. The subject information acquisition apparatus according to claim 1, further comprising:
a supporting mechanism configured to support the hermetic casing with an arm, wherein the hermetic casing is configured to be movable by the supporting mechanism.

4. The subject information acquisition apparatus according to claim 3, wherein the supporting mechanism includes a mechanism configured to change a posture of the hermetic casing in relation to the subject.

5. The subject information acquisition apparatus according to claim 1, further comprising:
a temperature adjusting unit configured to adjust a temperature of the acoustic matching liquid filled into the hermetic casing.

6. The subject information acquisition apparatus according to claim 1, wherein
at least a portion of the hermetic casing is formed of a light blocking member that blocks light from the irradiating member.

7. The subject information acquisition apparatus according to claim 1, further comprising:
a camera disposed inside the hermetic casing so as to capture images of a portion of the subject contacting the transmissive member; and
a monitor configured to display the images captured by the camera.

8. The subject information acquisition apparatus according to claim 7, wherein the monitor is provided on the hermetic casing in opposition to the transmissive member.

9. The subject information acquisition apparatus according to claim 1, further comprising:
a light source optically connected to the irradiating member.

10. The subject information acquisition apparatus according to claim 9, wherein the light source is a laser light source located outside the hermetic casing.

11. The subject information acquisition apparatus according to claim 9, further comprising;
a light guiding unit optically coupled to the light source and the irradiating member.

12. The subject information acquisition apparatus according to claim 11, wherein the light guiding unit includes at least any one of a fiber, a mirror and a prism inside the hermetic casing.

13. The subject information acquisition apparatus according to claim 1, further comprising:
a casing support member having a plurality of joints and a plurality of arms configured to movably support the hermetic casing on the subject.

14. The subject information acquisition apparatus according to claim 1, further comprising:
a handle secured to the hermetic casing configured to be grasped by an operator for moving the hermetic casing.

15. The subject information acquisition apparatus according to claim 1, wherein the transmissive member is secured to the opaque housing in sealing manner around the opening and configured to prevent the acoustic matching liquid from leaking outside.

16. The subject information acquisition apparatus according to claim 1, wherein the transmissive member is secured to the opaque housing in sealing manner around the opening such that the acoustic matching liquid is filled in the hermetic casing.

17. An apparatus comprising:
a casing having an opaque region and a transmissive region, the casing configured to store an acoustic matching material therein;
an irradiating portion disposed inside the casing so as to irradiate a subject with light via the transmissive region, such that an acoustic wave is generated from the subject;
an acoustic wave probe disposed inside the casing so as to receive the acoustic wave, propagated from the subject, through the transmissive region, and through the acoustic matching material between the transmissive region and the acoustic wave probe; and
a scanning mechanism disposed inside the casing so as to move the irradiating portion and the acoustic wave probe in relation to the casing,
wherein an optical transmissivity, with respect to the light irradiated from the irradiating portion, of the transmissive region is higher than an optical transmissivity of the opaque region.

18. The apparatus according to claim 17, further comprising:
a subject mounting unit on which the subject is placed, wherein the casing is configured to be movable in relation to the subject mounting unit.

19. The apparatus according to claim 17, further comprising:
a supporting mechanism configured to support the casing with an arm, wherein the casing is configured to be movable by the supporting mechanism.

20. The apparatus according to claim 19, wherein the supporting mechanism includes a mechanism configured to change a posture of the casing in relation to the subject.

21. The subject information acquisition apparatus according to claim 17, wherein the casing is a hermetic casing to store the acoustic matching material therein.

22. The apparatus according to claim 17, further comprising: a temperature adjusting unit configured to adjust a temperature of the acoustic matching material stored in the casing.

23. The apparatus according to claim 17, wherein at least a portion of the casing is formed of a light blocking member that blocks the light from the irradiating portion.

24. The apparatus according to claim 17, further comprising:
a camera disposed inside the casing so as to capture an image of the subject contacting the transmissive region of the casing; and
a monitor configured to display the image captured by the camera.

25. The apparatus according to claim 24, wherein the monitor is provided with the casing.

26. The apparatus according to claim 17, further comprising:
a light source optically connected to the irradiating portion.

27. The apparatus according to claim 26, wherein the light source is a laser light source located outside the casing.

28. The apparatus according to claim 26, further comprising;
   a light guiding unit optically coupled to the light source and the irradiating portion.

29. The apparatus according to claim 28, wherein the light guiding unit includes at least any one of an optical fiber, a mirror and a prism inside the casing.

30. The apparatus according to claim 17, further comprising:
   a casing support member having a plurality of joints and
      a plurality of arms configured to movably support the casing.

31. The apparatus according to claim 17, further comprising:
   a handle secured to the casing configured to be grasped by
      an operator for moving the casing.

32. The apparatus according to claim 17, further comprising a stage as the scanning mechanism, wherein the irradiating portion is synchronized with the acoustic wave probe by the stage.

\* \* \* \* \*